US007309161B1

(12) United States Patent
Eliasson

(10) Patent No.: US 7,309,161 B1
(45) Date of Patent: Dec. 18, 2007

(54) METHOD FOR DETERMINATION OF MAGNIFICATION IN A LINE SCAN CAMERA

(75) Inventor: Tracy K. Eliasson, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/552,545

(22) Filed: Oct. 25, 2006

(51) Int. Cl.
G01D 18/00 (2006.01)
G21K 5/10 (2006.01)
(52) U.S. Cl. .................................. 378/207; 378/146
(58) Field of Classification Search ................ 378/207; 702/150; 356/432–435
See application file for complete search history.

(56) References Cited

U.S. PATENT DOCUMENTS

| 4,260,898 A * | 4/1981 | Annis ........................ 378/146 |
| 5,418,832 A * | 5/1995 | Barnes ....................... 378/146 |
| 6,990,174 B2 * | 1/2006 | Eskelinen .................... 378/38 |
| 2004/0213380 A1 * | 10/2004 | Shaw et al. ................. 378/145 |

* cited by examiner

Primary Examiner—Edward J. Glick
Assistant Examiner—Irakli Kiknadze

(57) ABSTRACT

The magnification $M_{ref}$ for a line scan camera can be found by exploiting a difference in the way $M_{ref}$ affects the notion of 'focus' in the x and y directions. $M_{ref}$ enters into the calculations for selecting z while focusing in the y direction, but not in x. A thin opaque calibration target is provided at a convenient height in z called the reference plane, and has straight edges aligned parallel to the x and y directions. To find $M_{ref}$ the line scan camera forms images of the calibration target over a range of trial z values known to include the height of the calibration target. An arbitrary and possibly incorrect trial value $M_i$ of $M_{ref}$ is then assumed and many slices of the calibrations target are calculated. Within these slices the edge parallel to the x direction will be sharply defined for some $z_x$, while at some other $z_y$ the edge parallel to the y direction will be sharply defined. Make a note of $e_i = z_y$. Repeat these steps for some number different trial $M_i$ that cover the plausible range of $M_{ref}$. Now fit a curve (e.g., a quadratic) to the data set $\{(e_i, M_i)\}$, and find the y-intercept (where e=0). The associated value of M is the magnification $M_{ref}$ in the reference plane containing the calibration target, and we found it without knowing the actual length of any part of the calibration target.

14 Claims, 4 Drawing Sheets

METHOD FOR DETERMINATION OF MAGNIFICATION IN A LINE SCAN CAMERA

REFERENCE TO RELATED PATENTS

This application is related to the subject matter of U.S. Patent Application entitled PRECISE X-RAY INSPECTION SYSTEM UTILIZING MULTIPLE LINEAR SENSORS, Ser. No. 10/394,632 filed 21 Mar. 2003 by Gerald L. Meyer and assigned to Agilent Technologies, Inc. For brevity and the sake of completeness, PRECISE X-RAY INSPECTION SYSTEM UTILIZING MULTIPLE LINEAR SENSORS is hereby incorporated herein by reference.

INTRODUCTION AND BACKGROUND

The electronic assemblies of today, whether they be a large IC (Integrated Circuit) of a PCA (Printed Circuit Assembly) can posses an extraordinary degree of functionality. This has created issues related to initial testing and performance verification upon manufacture, as well as to periodic testing and performance verification during routine maintenance or trouble shooting and repair. In many cases, the old technique of having a test procedure followed by a trained technician that understands how the thing works is simply out of the question: the overwhelming complexity and issues of time and cost force us to seek other approaches.

In manufacturing large complex electronic assemblies the philosophy has tended toward one of ensuring that the design is sound, and then using good parts to correctly form the assembly. The expectation is that the completed assembly should work as desired. Associated with this is the notion that the sooner a defect can be discovered in the manufacturing process, the less it costs to discover and fix it. Some defects can only be discovered through performance testing, while others, especially those related to mechanical properties, can be discovered by inspection. Both performance testing and inspection can be automated to a significant degree. And since the effect on performance of a mechanical defect, such as a solder bridge between two traces on the PCA, or a break in a trace, might be pronounced ("It's dead and oozing stinky smoke . . . ") or subtle ("Every so often it does something goofy . . . "), and since finding a mechanically based electrical fault by analysis of electrical operation is like looking through the wrong end of a telescope, it is generally agreed that a through mechanical inspection should precede an attempt to operate the assembly.

Automated mechanical inspection of assembled PCAs turns out to be something that can be effectively accomplished. What one might call an "x-ray vision system" is proving to be an agreeable and cost effective way of reliably finding breaks in traces, bridges between traces, and voids in solder joints. Since x-rays are involved, these defects need not be upon an exposed surface to be discovered. The determination that a defect is present can be made by analysis of a suite of work images (say, for a solder joint) or by comparison of a work image with a stored exemplar (say, for trace integrity).

Such automated x-ray inspection systems have found acceptance in the marketplace, and new and refined techniques are appearing that both lower the cost and increase the capability of new automated inspection systems.

One of the ways to lower the cost of an x-ray imaging system is to reduce its mechanical complexity. One form for an early system used a circularly deflects x-ray beam and a rotating sensor. These items might be twelve to twenty inches away from each other, with the PCA disposed between them, but all must be in precision alignment if features (and defects) on the order of a few thousandths of an inch are to be resolved during testing. Such requirements add significantly to the mechanical complexity and cost of the imaging system.

An attractive alternative to such a design is one using a stationary line scan camera (1), such as is set out in the incorporated "PRECISE X-RAY INSPECTION SYSTEM . . . ", which we now summarize with the help of FIG. 1. As shown in FIG. 1, a plurality of multi-element imaging sensors (2) is disposed beneath a divergent x-ray 'point source' (3). The image sensors 2 may each be just one pixel wide, or may be several pixels wide for use with a TDI (Time Domain Integration) style line scan camera, and each has perhaps 2048 pixels uniformly distributed along a length of say, six to eight and one half inches. (The rationale for equating an imaging sensor one pixel wide and a TDI sensor several pixels wide arises from the fact that in either case, just one pixel value per clock cycle is produced for the TDI case, as if it were only one pixel wide—which it is not, so the pixel values produced are different, but still are just one value per clock cycle.) The image sensors may be similar to contact image sensors used in the visual scanning of documents, save that they include a thin covering of material that fluoresces (or scintillates) with visible light when excited by x-rays. The long axes of the image sensors are all parallel to one another, and we shall call this direction the x axis. The arrangement in x and y of the individual image sensors their plurality is not a particular issue here, and we show them as spread out over an area, there better to mimic the spatial aspects of an 'area' image sensor. And while not essential, it is convenient if they cover a contiguous portion of the x axis with no embedded gaps corresponding to where one sensor stops and another starts.

Before proceeding we should address an issue relating to terminology and the use of the term 'camera' in this setting. We are aware that some practitioners use the term 'camera' to refer to an individual multi-element imaging sensor, even if it is but one pixel in width (or more, for TDI applications), and that they would be inclined to refer to the overall line scan apparatus as the 'line scan system.' We find this somewhat cumbersome, as the term multi-element image sensor is perfectly descriptive, as is the notion of a camera whose output is an image representing a slice of the entire three dimensional object, and which happens to use a line scan technique upon multi-element imaging sensors that are one pixel wide, and which we shall be content to call a 'line scan camera.'

We shall arrange that the location from which the x-rays (4) emanate is above a central location within the arrangement of imaging sensors, and that the x-rays diverge uniformly in a generally conical manner toward the imaging sensors. The imaging sensors are all mounted with uniform height at known locations within a plane (5) that is perpendicular to the axis of the conical dispersion of the x-rays. We may assume, in the absence of any intervening material that absorbs or block x-rays, that each pixel location in the generally circular array of image sensors receives roughly the same level of x-ray illumination, and that each produces about the same level of electrical signal. (We also expect that any signal variations occurring under such 'neutral' conditions have been noted, and can if desired, be removed from measured data as effects of offsets and scaling, to leave in place indications related only to conditions within a PCA being tested.)

A PCA (6) to be tested is interposed between the x-ray source and the imaging sensors, and is generally parallel to the plane 5 of the imaging sensors. The size of the PCA may exceed that of the planar array of imaging sensors by many times over, and to accommodate that as well as allow each image sensor to 'see' every feature of interest on the PCA, the PCA is translated at a generally uniform velocity ($V_{scan}$) along a serpentine path 9 that is known in advance and under the control of a transport control mechanism (8), which may be a computer programmed and connected to operate in this manner. This is primarily smooth continuous motion back and forth along the y direction, with intervening discrete steps in the x direction at the extremes of y motion. During portions of the serpentine path when x-ray shadows of interest fall on the imaging sensors, the data signals from the imaging sensors (denoted by the lower case Greek α) are read out at a regular clock rate and stored in a (rather large!) memory (7). Thus, at the end of a serpentine scan we have a whole big bundle of data that can be algorithmically manipulated (8) with software executed by a computer to produce (8) images of interest, and which may then be analyzed in isolation or compared to one or more exemplars, and in any case evaluated (10) using selected criteria. These techniques for analysis and comparison are conventional, and are not of further interest here.

Our interest lies more in an aspect of the manner in which an image is obtained in the first instance. To assist us in this, we may reduce the scope of the above described activity to obtaining a partial image along just one portion of one y-direction leg of the serpentine with data from just one imaging sensor. [This is done with the understanding, of course, that what we do for one imaging sensor we also do for the others, and that there are known ways for the processed data for the various sensors to be combined to produce a 'recontructed' (think: 'complete') image of interest.]

To continue, we note that a notion of 'in focus' can be developed. Consider some pixel position along some imaging sensor. It basically represents all or a portion of an x-ray shadow of some target feature on the PCA that lies along the line (ray trace) from that pixel position to the origin of the x-rays (assumed to be a bright point-like spot). As the PCA moves, several values for our pixel location are clocked out and captured. These values are for different locations in y but at the same location (i) in x. Let's call such a thing a 'Y alpha sequence at (some) X,' or $Y\alpha@X_i$. At the same time this is also happening for other pixel locations on the same imaging sensor (at another value of i for $X_i$), and at the corresponding pixel location (if there is one at the x) on all the other imaging sensors. The arrangement of imaging sensors is such that at least one other imaging sensor will eventually produce a sequence of signals (various α values) for that same target feature. ('Eventually' might mean at a different location on the same leg of the serpentine, or on a different leg).

Now, for all the other imaging sensors that produced a sequence of signals for the target feature (which might well be all of them), place the elements of these various $Y\alpha@X_i$ into correspondence: this element of the sequence from this sensor corresponds to that element of the sequence from another sensor, and so on. We note that these elements (various α values) were probably not obtained at the same time, as the feature might have been imaged at a different place along the serpentine path. The important thing is to agree that such a correspondence between 'the same location in x' on different imaging sensors exists, and the effects of sensor separation can be represented as shifts or offsets of element positions between the sequences: a shift (or offset) of so many elements between a $Y\alpha@X_1$ and a $Y\alpha@X_2$, and of a different number of elements between $Y\alpha@X_1$ and a $Y\alpha@X_3$, and so on.

A similar correspondence can be formed with shifts between different pixel locations in x that 'have the same y,' whether they are on the same imaging sensor or on two that each lie on the other's axial extension (along the x axis or along a line parallel to it). That is, the data also contains various instances of an 'X alpha sequence at (some) Y,' or, $X\alpha@Y_j$. (A note about notation is in order here. We will write $Y\alpha@X_i$ and $X\alpha@Y_j$ instead of $Y\alpha@X_i$ and $X\alpha@Y_i$, lest it appear that when considering these two at the same time the subscript i is a common value for each. When we write $Y\alpha@X_i$ and $X\alpha@Y_j$, each of i and j are allowed to range independently, and might be the same or might be different, as the case requires. What we mean is no more or no less than just 'some X' and 'some Y.')

A moment's thought will confirm the assertion that the height of the target feature above the imaging sensors also has an effect (discussed below in connection with magnification, M) in that it determines how far apart in the imaging plane two shadows along different diverging rays fall upon the imaging plane.

Now, if we pick from some $Y\alpha@X_i$ and $X\alpha@Y_j$ that contain a common element that belongs to (is contained) in the target feature, and with knowledge of sensor separation and a desired height in z, we 'properly' shift their respective other $Y\alpha@X_i$ and $X\alpha@Y_j$ into correspondence with them and then combine (say, by averaging) all instances of that element (for the target feature) for all the sequences, we can favor the desired location along the z axis in that: For all the ray traces passing through the target feature at that z and reaching an image sensor, each has a signal value α related to the target feature, and we may take their average as representative thereof, while for other rays that might reach a sensor after passing through a different z location the associated signal values tend to cancel each other (average out). Note that: which pixel position along the length of a sensor has determined an x coordinate (as further understood by which leg in the serpentine the PCA was happening when that pixel value was taken); the location within the sequence of clocked out sensor values (which $\alpha_j$) within a leg determines the y coordinate; and, the desired z coordinate further affects the pattern of shifts or offsets between the $Y\alpha@X_i$ and $X\alpha@Y_j$ from for the imaging sensors. The averaged value obtained here is the value of the pixel at (x, y, z), i.e., its intensity, which we might call A (the Greek upper case alpha).

We have just found (x, y, z, A), or a pixel description for a location in space, which might belong to a solder ball affixing a huge IC to a ball grid array. We do this for not just one pixel location, but for all pixel locations that may be of interest (there might be parts of a PCA that we do not bother to inspect). That is, we can pick an (x, y) location and then shift in x as y remains fixed, and then shift in y as x remains fixed. Then we pick another (x, y) location, and so on. What emerges is an (x, y) image in A at some height in z. We probably want the same (x, y) regions at other values for z, as well, and it will be appreciated that in this general manner a desired complete two or three dimensional image can be constructed. The serpentine path serves to cover the entire PCA, while an increased plurality of imaging sensors provides improved cancellation of the 'out of focus' planes in z.

Before leaving this somewhat simplified description of how a line scan camera operates, we should point out a few other details that will be of interest in what follows. The topic is: "How do we know how much to shift (or offset) the elements of the various sequences from the associated imaging sensors?" Hmm. Well, on the one hand we know the relative position of each imaging sensor with respect to all the others (or at least we believe so . . . ). It turns out that, given the measurement precision that the x-ray line scan camera is otherwise capable of, we are well advised if we become suspicious of the effects of temperature change. Furthermore, as the next few paragraphs show, there is a particular magnification parameter called $M_{ref}$ that is also rooted in the mechanical aspects of the whole line scan camera.

With reference now to FIG. 2, it will be appreciated that as the divergent x-rays 4 spread out on their journey from the x-ray spot on the source 3, a given sized target object (12) in the PCA will create a larger shadow 13 (in spatial terms measured in pixel-to-pixel spacings at the imaging sensor) if the target object is closer (11) to the x-ray spot on the source, than it does (14) when further away (15). The ratio between the actual size of the target object and its apparent size according to the corresponding shadow on the sensor (and, of course, taking the spacing of the sensor elements into account) is called the magnification, or M. We are most interested in knowing an accurate value of M for out instances of testing, as it figures in how much to shift the sequence of measured α values from each sensor to correspond to those of another sensor, or to shift a sequence of α values from a given sensor element for combination with the un-shifted sequence for the same sensor element, and thus 'focus' at a desired value of z.

Now, when we shift one collection of α values to combine with another, one collection moves relative to the other: it won't do if they both move the same amount, as the net effect would be no shift at all. So, if there are several collections to be shifted by different amounts and then combined, we can appreciate that all of these can be thought of as being shifted by the requisite amount relative to something that does not shift. That 'something' is the image, or slice, (which is some collection of α values) at some z height of convenience, say, $z_k$. We shall refer to this height $z_k$ in z as the reference plane. When consider what magnification M is afoot for the focusing of reconstructed images, the necessary shifting will be performed relative to $z_k$, and the value of M that arises from using that particular value for z will be called $M_{ref}$.

Now, it is not so much that we don't have a general idea of what $M_{ref}$ is, or that $M_{ref}$ changes abruptly from day to day as the system is in use. A given x-ray line scan camera has a certain $M_{ref}$. It is more that it would be rash to operate the system for weeks or months at a time and expect $M_{ref}$ to remain absolutely constant. Or to expect that mechanical wear, adjustment and other maintenance do not affect $M_{ref}$. It has been found that an x-ray line scan camera of the sort described here has sufficient resolution and accuracy that modest changes in temperature can produce detectable changes in the effective value of $M_{ref}$. But our ability to know where in z an image is located (and this is the stock in trade of an 'x-ray vision' PCA inspection system) depends on knowing $M_{ref}$! Indeed, if $M_{ref}$ is too far off, images will not appear to be in focus at all, owing to significant subversion of the shift and average technique used to cancel out that which is 'out of focus' and leave just that which is 'in focus.' We believe that it is prudent to find $M_{ref}$ whenever the system is powdered up, after maintenance, perhaps at least once or twice a day whether it needs it or not, and at any other time when it seems like a good idea.

There are prior art solutions to discovering an actual value of $M_{ref}$ for a particular line scan camera system. For example, the measured distance between two index lines or marks can be compared to what is thought to be their true distance. Unfortunately, the limits imposed on measurement precision by the pixelation of the image sensors, and the uncertainty of other system variables conspire to limit the accuracy with which the true value of $M_{ref}$ can be discovered by this method. What we need is a better way to easily discover the true value of $M_{ref}$ whenever it seems useful to do so. How to do it?

SIMPLIFIED DESCRIPTION

The magnification $M_{ref}$ for a line scan camera can be found by exploiting a difference in the way $M_{ref}$ affects the notion for 'focus' in the x and y directions. It turns out that $M_{ref}$ enters into the calculations for selecting z while focusing in the y direction, but not in x. A calibration target is provided at a convenient height in z, and which may or may not be that particular height $z_k$ we call the reference plane. It is preferred that physically, the calibration target be part and parcel of the transport mechanism that carries the PCAs as they are interposed for serpentine movement between a stationary point source of divergent x-rays and a stationary plane of imaging sensors, and that the calibration target is permanently affixed thereto and not part be of any PCA. The calibration target is thin and opaque to x-rays (e.g., of tungsten), and has a straight edge aligned parallel to the x direction and a straight edge aligned parallel to the y direction. These may be two sides of an isosceles right triangle shape removed from a square of tungsten. The tungsten square is planar and is parallel to the imaging plane. To find $M_{ref}$ the line scan camera forms image of the calibration target over a range of z values known to include the height of the calibration target. An arbitrary (and possibly either correct or incorrect) or perhaps a known incorrect trial value $M_i$ of $M_{ref}$ is then assumed and many slices of the calibration target are calculated. Within these slices the edge parallel to the x direction will be sharply defined for some $z_x$, while at some other $z_y$ the edge parallel to the y direction will be sharply defined. Make a note of $e_i = z_x - z_y$. Repeat these steps for some number (e.g., thirty or fifty) different trial $M_i$ that cover the plausible range of $M_{ref}$. Now fit a curve (e.g., a quadratic) to the data set $\{(e_i, M_i)\}$, and find the y-intercept (where e=0). The associated value of M is the magnification in the reference plane containing the calibration target, and we found it without knowing the actual length of any part of the calibration target.

DETAILED DESCRIPTION

We turn now to a topic that provides the basis for a technique of discovering the magnification $M_{ref}$ in a line scan camera, and which does not rely upon advance knowledge of the particular dimensions of a calibration target that is imaged as part of the discovery process. That 'topic' is the observation that the 'shift and add/average' operation used to 'focus' a slice at a particular z value is a function of $M_{ref}$ for such operations on an $Y\alpha@X_i$, but not for those operations on an $X\alpha@Y_j$. Said another way, this means that we need to use an $M_{ref}$ (i.e., "know it") to get 'focusing' to happen for the $Y\alpha@X_i$, but that no such $M_{ref}$ is needed for the $X\alpha@Y_j$. Leaving a demonstration of that assertion aside for just a moment, if we accept it as true we can exploit that idea by imaging a calibration target that has co-planar straight-line edges that are parallel to the x and y axes and in a plane parallel to the imaging plane, and noting when the edges appear to be 'sharp,' or well defined, as $M_{ref}$ is varied during a suite of trial imaging operations. The value of $M_{ref}$ that causes the 'best edge' simultaneously in both x and y is the sought after actual value of $M_{ref}$ for the imaging system.

We now undertake a demonstration of why focusing for $Y\alpha@X_i$ is a function of $M_{ref}$, while focusing in $X\alpha@Y_j$ is not. The short answer is this: Projected image size (in pixels) in the x direction is function of $M_{ref}$ for reasons illustrated in FIG. 2, because when data is clocked out from the imaging sensors the entire projection of a feature falls on the sensors (or at least would if it is not too big . . . ). The divergence of the x-rays, over the distance traveled, produces an expansion $M_{ref}$ of the imaged feature; and we note that the the greater the expansion, the more x direction pixel positions are involved in representing the size of the feature, and that any single clocking of the sensor reveals them all to at once. In contrast, the projected image size in pixel locations along the y direction is only a function of how often the data is clocked out of the imaging sensors for any given velocity of the feature being imaged.

Figure 1:
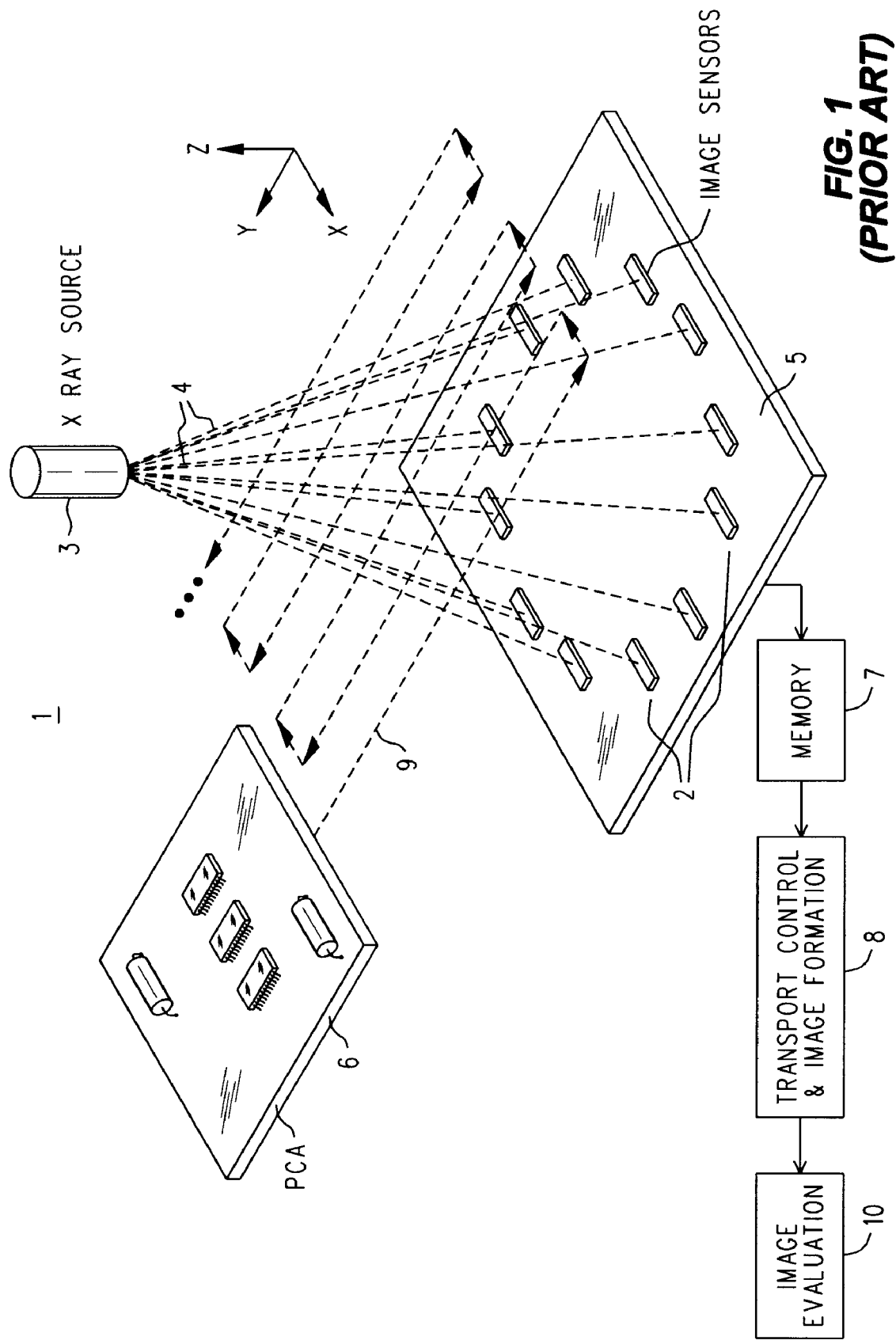
FIG. 1 is a simplified perspective view of certain overall aspects of an x-ray line scan camera system for the automated inspection of PCAs.
Figure 2:
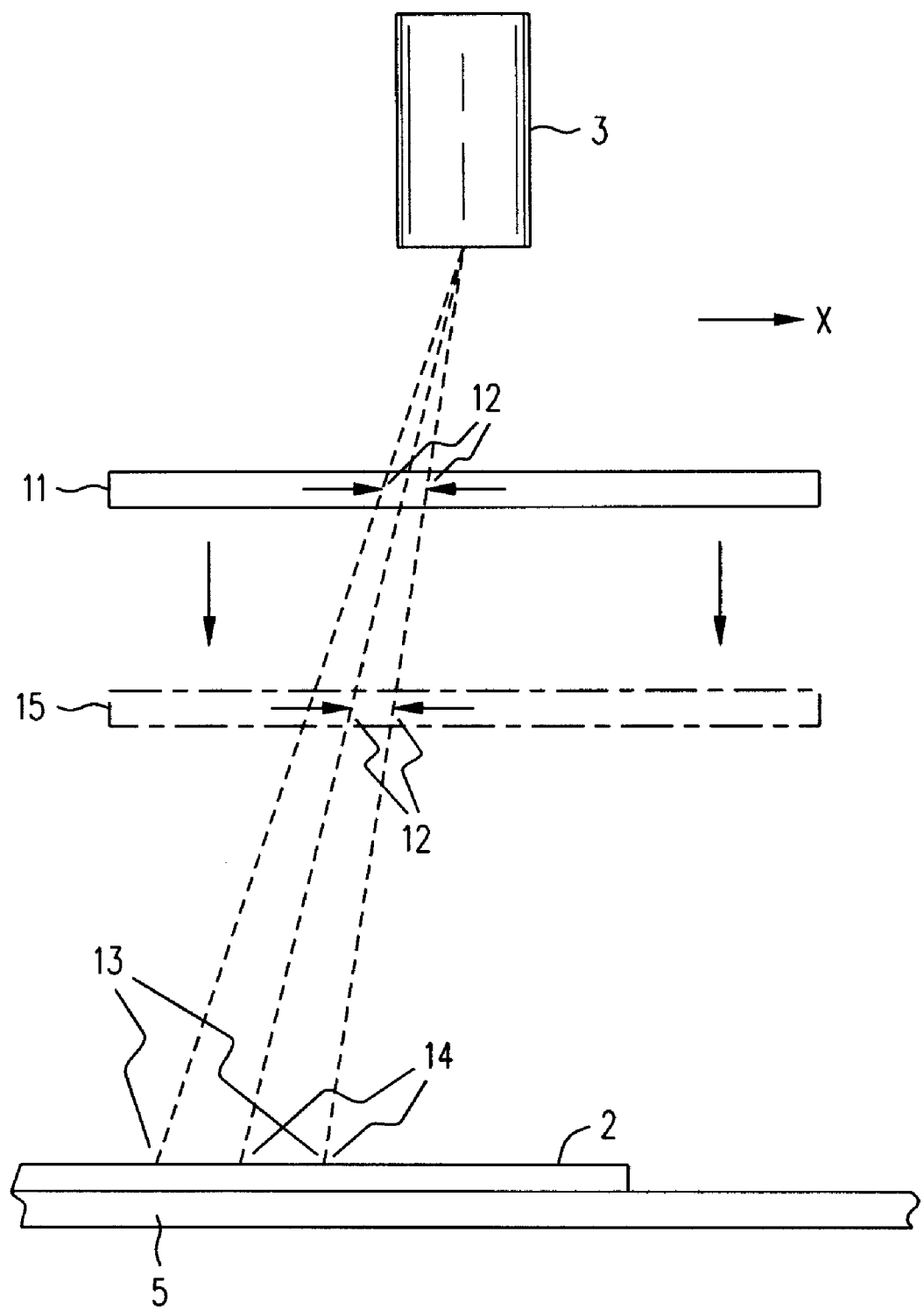
FIG. 2 is a simplified mechanical schematic diagram of a portion of the system of FIG. 1 and illustrating the notion of magnification $M_{ref}$ that is a function of a height in the z direction.

FIG. 2 serves to support the notion that $M_{ref}$ is involved in the focusing operations of 'shift and add' for the $Y\alpha@X_i$; $M_{ref}$ affects the number of pixels needed to represent the projection of a feature, and experience suggests that appreciation of that idea is not difficult. On the other hand, experience also suggests that the notion that $M_{ref}$ does not figure in the 'same' focus operations for the $X\alpha@Y_j$ is not intuitive, and we turn now to FIG. 3 to show why such independence from $M_{ref}$ is indeed the case.

Figure 3:
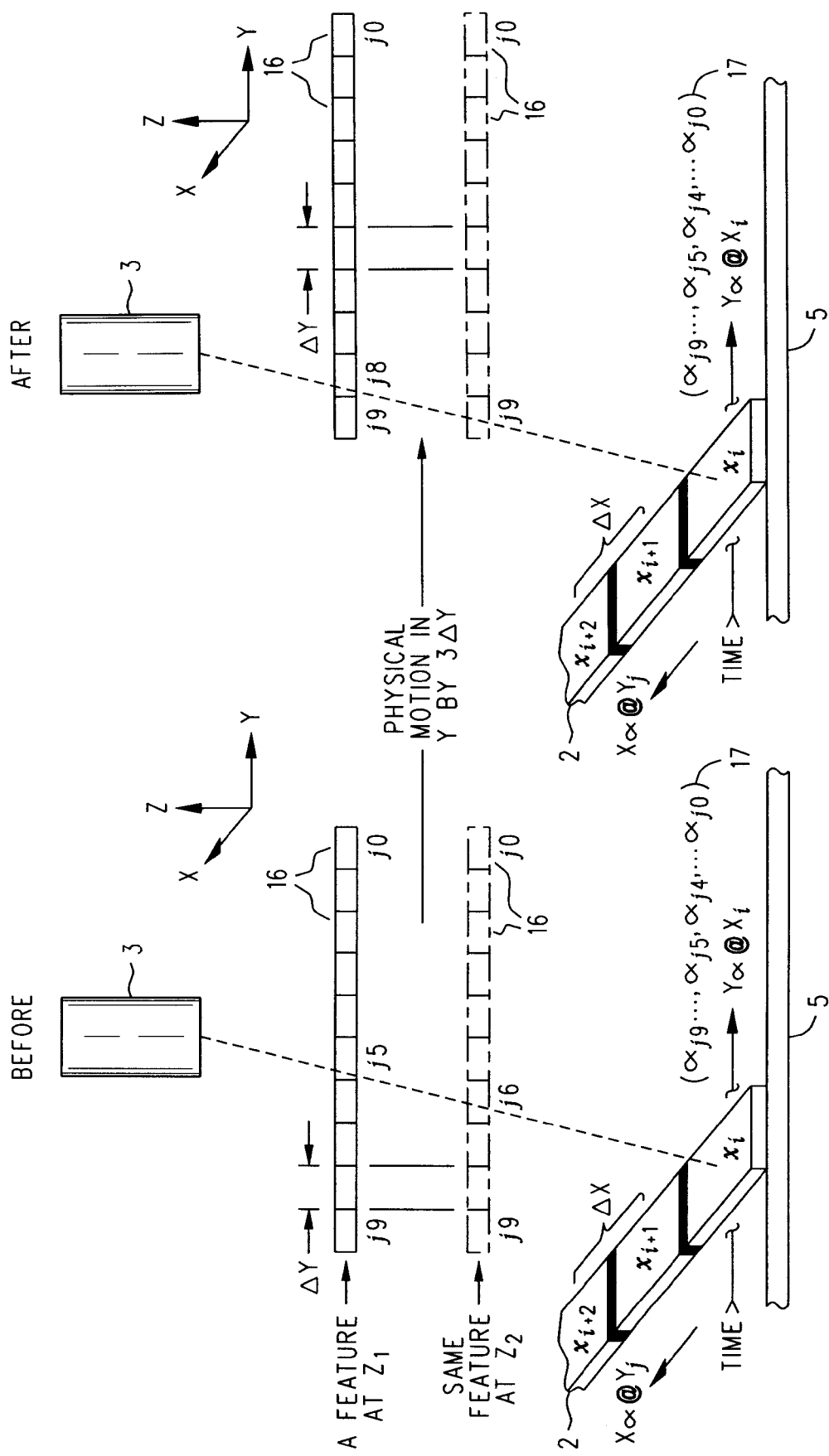
FIG. 3 is a simplified diagram similar to FIG. 2, save that it is for scanning in the direction in which the PCA is moved by a physical transport mechanism, and does not exhibit magnification $M_{ref}$ that is a function of height in the z direction.

With reference now to FIG. 3, let us suppose that we image the same feature (16) at two different z heights, $z_1$ and $z_2$. In a setting such as FIG. 2 we would expect to get, and indeed would get, different numbers of pixel locations (along the y axis) on the image sensor at the two different projections of the feature onto the sensor. That happens because the sensing element are really 'all there,' under the projection of the diverging x-rays. But, as is shown in FIG. 3, along the x axis direction there is a width of just one sensing element, and the only thing that causes change in what that sensing element reports to the outside world about x axis activity is how often it is clocked and the velocity of the feature.

Here in detail, is how to appreciate FIG. 3. On the left side of FIG. 3 is a 'BEFORE' scenario, and on the right is an 'AFTER' scenario. In each case we are imaging the same feature 16 on the same PCA. BEFORE shows doing the imaging at height $z_1$ and again also at $z_2$, and in each case the location of the x-ray beam has progressed to about half-way between the opposite ends of the feature 16. We are not suggesting that both heights could be imaged at once; instead, they are shown together because even if they are done at different times the operation is, in a schematic sense, identical except for the difference in z. The same remarks apply to the AFTER half of the figure, which depicts the situation after clocking out three additional values of $\alpha_i$ subsequent to the situation of the BEFORE scenario. The PCA is moving with some generally constant velocity $V_{scan}$ in the y direction. Let us say for the sake of a definite example that the feature 16 is ten samples long in the y direction. Thus, there will be ten $\Delta y$s, and every amount of movement by $\Delta y$ is accompanied by a new value of $\alpha_j$ from the sensor's element for $x_i$. We thus expect a sequence of $Y\alpha@X_i$ that has ten values, or: $\{\alpha_0 \ldots \alpha_9\}$. We can learn what we need to about $M_{ref}$ from examining what $\alpha_i$ emerge for $x_i$, and need not investigate the other $\alpha$ sequences for the other $x_{i+1}$, as we would just learn the same thing, and the increased complexity for the necessary notation is simply not worth the effort.

With regard to the 'generally constant' velocity mentioned in the preceding paragraph, there are at least two possibilities. One would be that the actual velocity of the PCA ($V_{scan}$) is really constant, and we create $\Delta y$ by observing transitions in a clock signal of constant frequency. Another, and perhaps preferable, arrangement is to allow $V_{scan}$ to be 'unregulated' and detect amounts of PCA motion that are $\Delta y$ in size, and clock the imaging sensor 2 upon such detection.

The next step in considering FIG. 3 is to note the sequence 17 $Y\alpha@X_i$ for the imaged feature 16 at height $z_1$. If the feature 16 is divided by sampling into j=10 regions, and ordered as from j=0 to j=9, then the sequence 17 is some series of j-many $\alpha_i$ each dependent upon the opacity to x-rays for those respective samples: $\{\alpha_{j9}, \alpha_{j8}, \alpha_{j7}, \ldots, \alpha_{j2}, \alpha_{j1}, \alpha_{j0}\}$. Other than noting what this sequence is, there is nothing else remarkable about it (except perhaps to notice that since the portion of feature 16 at j=0 was imaged and its corresponding $\alpha_{j0}$ clocked out first, we put $\alpha_{j0}$ on the far right of a customary time axis running from left to right . . . ).

Now consider the same feature 16 at height $z_2$. Although the sequence $\{\alpha_{j9}, \alpha_{j8}, \alpha_{j7}, \ldots, \alpha_{j2}, \alpha_{j1}, \alpha_{j0}\}$ for $z_2$ is produced at different clock cycles relative to the mechanical motion of the PCA past some fixed point of reference when compared to $z_1$, it is still identical sequence 17 as was obtained for operation at height $z_1$. Therefore, the height in z, and hence $M_{ref}$, does not affect focusing in the y direction, as we have the same sequence of $\alpha_i$ data to work with in each case.

Figure 4:
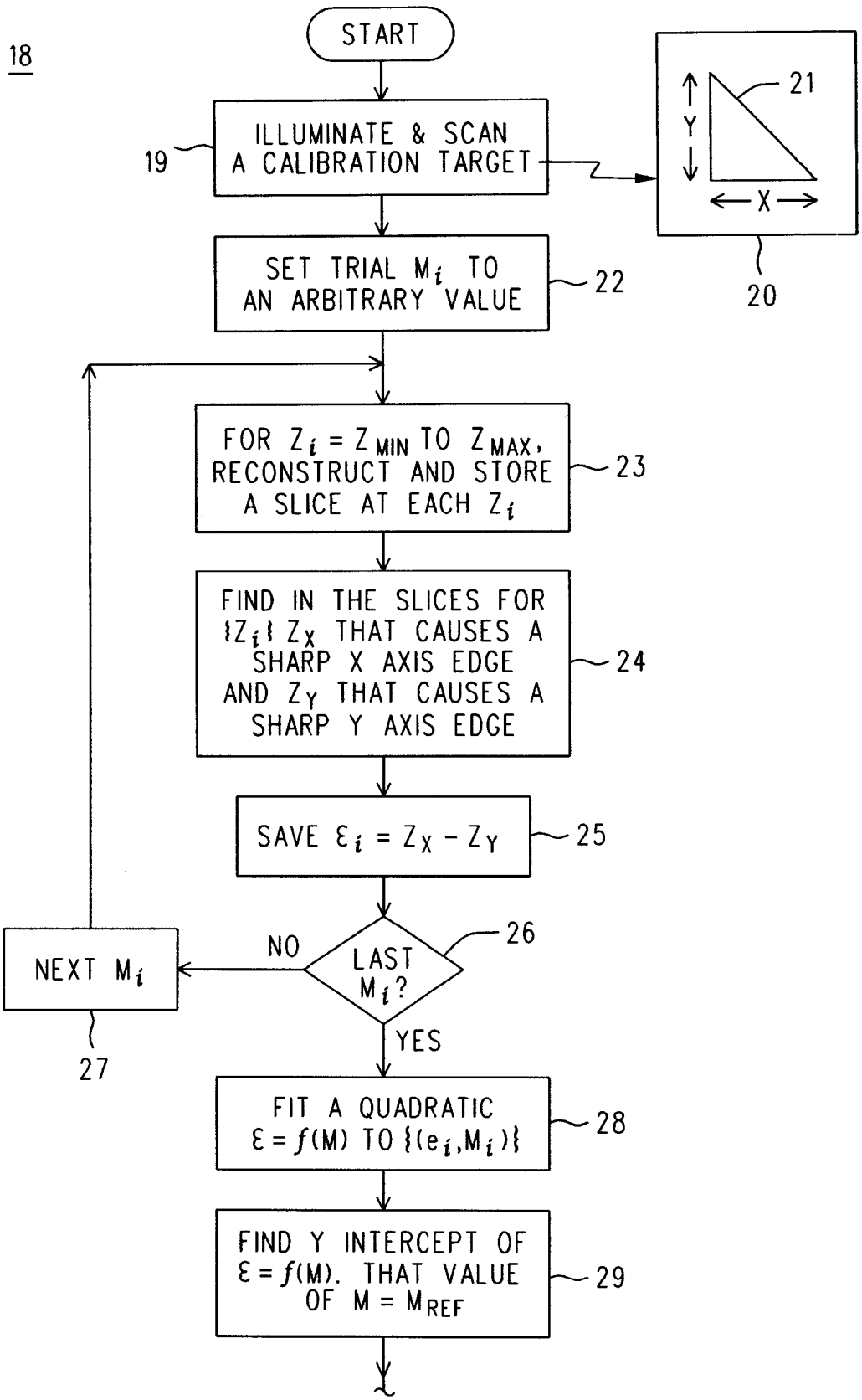
FIG. 4 is a simplified flowchart of a method for discovering a particular value of $M_{ref}$ usable in all $z_i$ without knowing in advance the actual size of a calibration target.

Refer now to FIG. 4, which is a simplified flowchart 18 of a procedure that discovers during a calibration activity a value of M ($M_{ref}$) that may be used for general line scan camera use during the actual line imaging and testing of production PCAs. The method of doing this discovery according to the flowchart 18 does not depend upon the measurement of known lengths in either of the x or y directions, and experience has shown that it is actually more accurate in discovering $M_{ref}$ than is an attempt to measure a known length.

The first step 19 in flowchart 18 is to scan a calibration target, such as the one 20 illustrated in the inset next to step 19. Although other calibration targets are possible, the one shown in an actual one used with good success, and is a right isosceles triangle void or cutout 21 whose equal edges are each fifty mils long and respectively parallel to the x and y axes, the triangular void or cutout located within the central portion of a square (or other shape containing the cutout) of tungsten, say, 2 mils thick. It is the edges of the cutout 21 in the x and y directions that we will be interested in, and with that in mind it will be appreciated that there are other shapes that may be used in the same manner as set out below. In any event, the scanning of step 19 is the creation of an entire collection of $X\alpha@Y_i$ and $Y\alpha@X_i$ in the vicinity known to contain the calibration target 20. Once we have such a collection of $X\alpha@Y_j$ and $Y\alpha@X_i$ we can variously 'put them in focus' at a collection some $\{z_i\}$ without any further scanning steps.

Now, the operation of 'putting them into focus at some instance of $z_i$' requires some value of $M_{ref}$. That, of course, is what we don't know in particular, although (absent some pernicious malfunction) we can almost certainly say that $M_{ref}$ we seek is between some $M_{min}$ and an $M_{max}$. And, as a reminder, according to the discussions of FIGS. 2 and 3, if we have picked some $z_i$ and discover that some trial $M_i$ (or vice versa) provides 'in focus' images in both the x and y directions, then we have found a value of $M_i$ that we are justified as taking as $M_{ref}$. To make just such a discovery is the purpose of flowchart 18 of FIG. 4.

The next step 22 is to set or select an arbitrary trial value for $M_i$. The selected value might accidently be the 'right' value (chances of that are slim) or it might (much more likely) be a 'wrong' value. Either way, it won't matter, as we are going to try a whole bunch of them, anyway. We might even pick an $M_i$ that is a known wrong value, say, either $M_{max}$ or $M_{min}$. Now at step 23 we cycle through all the various values of $z_i$ from a $z_{min}$ to a $z_{max}$ (reasonable conservative values for which are known ahead of time because of where the calibration target 20 has been placed— it is a permanent part of the imaging system's transport mechanism and not part of a PCA that might have some defect). Now, for the set of values $\{z_i\}$ there will be a $z_x$ that appears to created the 'in focus' condition along the x direction for the trial $M_i$ at hand, and there will be a $z_y$ that appears to create the 'in focus' condition along the y direction for that same trial $M_i$. But unless that $M_i$ is also $M_{ref}$, $Z_y \neq z_x$, and conversely, if $z_y = z_x$, then $M_i$ is $M_{ref}$.

There are various known ways that the condition of 'a sharp edge' for an image expressed in pixels can be determined. The technique preferred here, and that has been found to be entirely satisfactory, is one based on the notion of taking the variance of the image with the edge after convolution of the image with a Sobel edge detection procedure. This involves pairs of alternate row and alternate columns in the pixel level description, and looking for pronounced differences. This is a known technique, and those wishing further information about how it works and how to do it may refer to one of the standard text on the matter: e.g., Machine Vision by Ramesh Jain, Rangachar Katsuri and Brian g. Schunck, published in 1995 in McGraw-Hill. The explanation of the Sobel technique in this edition of that work will be found at pages 147-148. It will be appreciated that this is but one of several techniques that may be used in support of performing step 24.

Step 24 is the enquiry about equality for the above described $z_x$ and $z_y$, for all of the slices created a step 23 for the various $z_i$. At step 25 we find and save the difference (an error $e_i$ in the trial $M_i$) between the $z_x$ and $z_y$ associated with each $z_i$. We write $e_i = z_x - z_y$, although we could have just as easily written either of:

$e_i = z_y - z_x$ or $e_i = |z_y - z_y|$, etc.

Now, at step 26 we enquire if we have done steps 23, 24 and 25 for the last $M_i$ in the collection thereof. If not, then the NO branch of the qualifier leads to step 27, where the next value of $M_i$ (in some convenient ordering thereof) is instituted, and steps 23, 24 and 25 are repeated until the last $M_i$ has been used in those steps. At that point the YES branch from qualifier 26 leads to step 28.

At step 28 a convenient form of function is fitted to the mapping described by the set of points $\{(e_i), (M_i)\}$. For example, a quadratic function for f has been found to be satisfactory. Now at step 29 we find the y intercept for e=f (M) (i.e., where e=0), and we have accordingly discovered the value of $M_i$ that equal $M_{ref}$. Subsequent to that discovery, the line scan cameras can be put to use in a production sense with confidence that with $M_{ref}$ used as the value for magnification, all slices at various $z_i$ for PCAs under test will be in focus for both the x and y directions.

Finally, it will be appreciated that a line scan camera uses actinic radiation to produce the $Y\alpha_i@X_i$ and $X\alpha_i@Y_j$ that are responsive to the amount of actinic radiation reaching the individual imaging sensor elements and that these $Y\alpha_i@X_i$ and $X\alpha_i@Y_j$ are focused at desired slices represented by a value for $z_i$ by shift and accumulate techniques. In the case where a workpiece to be imaged is a PCA the actinic radiation may be x-rays, as previously described. It will be further appreciated that if the workpiece is transparent to some wavelengths of visible light, or perhaps ultra violet or infrared light, then the actinic radiation could be of such a wavelength. All that we should further attend to is that the calibration target has the requisite properties of opacity for the actinic radiation in use, as well as the edges herein bordering transparent regions which are parallel to the x and y aces.

It will be further appreciated with respect to the foregoing, that the discovery of $M_{ref}$ can be performed with just one imaging sensor, provided that it is either long enough so that a single scan will cover the entire object to be imaged, or if not, a suitable serpentine or other scan pattern is employed. Furthermore, the placement of the imaging sensors (2) within the imaging plane (5) may be arbitrary (i.e., random, or at least irregular), or regular. 'Regular' means in accordance with some regular or symmetrical geometrical figures, such as equally spaced locations around the perimeter or circumference of a circular or elliptical shape, or at the vertices of a regular polygon.

I claim:

1. A method of determining the magnification $M_{ref}$ for a line scan camera that transports a work piece to be imaged in orthogonal x and y axis directions while at a fixed height along a z axis normal to the x-y plane containing the x and y axes, the method comprising the steps of:

(a) transporting at a fixed location $z_{cal}$ along the z axis and in the y axis direction a calibration target having opaque edges parallel to the x and y axes and both opaque edges in a plane parallel to the x-y plane;

(b) while performing step (a), illuminating the calibration target with actinic radiation emanating in a generally uniform conical pattern from a point source and in a direction toward the calibration target and then further toward a multiple element detector of the actinic radiation disposed upon a detection plane parallel to the x-y plane, the conical pattern having an axis normal to the detection plane, and the multiple element detector having a plurality of $x_i$ detection elements responsive to the actinic radiation along a line parallel to the x axis;

(c) while performing step (b), collecting and storing at regular intervals of transport motion in step (a) the plurality of detection element outputs $Y_j\alpha@X_i$ that, at successive locations $y_j$ $\Delta y$ apart along the y axis, are the respective outputs $\alpha$ of an $i_{th}$ detection element $x_i$ of the multiple element detector having some location along the x axis within the detection plane;

(d) while performing step (b), collecting and storing at regular intervals of transport motion in step (a) the plurality of detection element outputs $X_i\alpha@Y_j$ that, at successive locations $\Delta x$ apart along the x axis, are the respective outputs $\alpha$ of each $i_{th}$ detection element $x_i$ of the multiple element detector having some location along the y axis within the detection plane;

(e) selecting an arbitrary trial magnification value $M_i$ from among a range of possible magnification values;

(f) while a trial magnification value $M_i$ is in effect:

(f1) subsequent to each instance of step (e), for each $z_i$ in a range from a selected $z_{min}$ along the z axis and by steps of a $\Delta z$ toward a selected $z_{max}$ along the z axis, $z_{min}<z_{cal}<z_{max}$, reconstructing the image at the height $z_i$;

(f2) subsequent to each instance of step (f1), inspecting the reconstructed image for $M_i$ for a value $z_x$ of $z_i$ that exhibits a sharp x axis edge and a value $z_y$ of $z_i$ that exhibits a sharp y axis edge;

(f3) subsequent to each associated instances of steps (f1) and (f2), saving a value $e_i$ that is indicative of the difference between the associated $z_x$ and $z_y$;

(f4) subsequent to steps (f1), (f2) and (f3), selecting an unused next value for $M_i$ until a selected number of different $M_i$ have been in effect;

(g) fitting a function $e=f(M)$ to the set of data $\{(e_i), (M_i)\}$; and (h) finding the y intercept $M_j$ of $e=f(M)$ and taking $M_j$ to be the value of $M_{ref}$.

2. A method as claim 1 wherein step (a) comprises motion in a serpentine pattern having legs parallel to the y direction and that are each a step apart in the x direction.

3. A method of determining the magnification $M_{ref}$ for a line scan camera that transports a work piece to be imaged in orthogonal x and y axis directions while at a fixed height along a z axis normal to the x-y plane containing the x and y axes, the method comprising the steps of:

(a) transporting at a fixed location $z_{cal}$ along the z axis and in the y axis direction a calibration target having opaque edges parallel to the x and y axes and both opaque edges in a plane parallel to the x-y plane;

(b) while performing step (a), illuminating the calibration target with actinic radiation emanating in a generally uniform conical pattern from a point source and in a direction toward the calibration target and then further toward a plurality of multiple element detectors of the actinic radiation arranged in a detection plane parallel to the x-y plane, the conical pattern having an axis normal to the detection plane, and each multiple element detector having a plurality of $x_i$ detection elements responsive to the actinic radiation along a line parallel to the x axis;

(c) for each multiple element detector and while performing step (b), collecting and storing at regular intervals of transport motion in step (a) the plurality of detection element outputs $Y_j\alpha@X_i$ that, at successive locations $y_j$ $\Delta y$ apart along the y axis, are the respective outputs $\alpha$ of an $i_{th}$ detection element $x_i$ of the multiple element detector having some location along the x axis within the detection plane;

(d) for each multiple element detector and while performing step (b), collecting and storing at regular intervals of transport motion in step (a) the plurality of detection element outputs $X_i\alpha@Y_j$ that, at successive locations $\Delta x$ apart along the x axis, are the respective outputs $\alpha$ of each $i_{th}$ detection element $x_i$ of the multiple element detector having some location along the y axis within the detection plane;

(e) selecting an arbitrary trial magnification value $M_i$ from among a range of possible magnification values;

(f) while a trial magnification value $M_i$ is in effect;

(f1) subsequent to each instance of step (e), for each $z_i$ in a range from a selected $z_{min}$ along the z axis and by steps of a $\Delta z$ toward a selected $z_{max}$ along the z axis, $z_{min}<z_{cal}<z_{max}$, reconstructing the image at the height $z_i$;

(f2) subsequent to each instance of step (f1), inspecting the reconstructed image for $M_i$ for a value $z_x$ of $z_i$ that exhibits a sharp x axis edge and a value $z_y$ of $z_i$ that exhibits a sharp y axis edge;

(f3) subsequent to each associated instances of steps (f1) and (f2), saving a value $e_i$ that is indicative of the difference between the associated $z_x$ and $z_y$;

(f4) subsequent to steps (f1), (f2) and (f3), selecting an unused next value for $M_i$ until a selected number of different $M_i$ have been in effect;

(g) fitting a function $e=f(M)$ to the set of data $\{(e_i), (M_i)\}$; and (h) finding the y intercept $M_j$ of $e=f(M)$ and taking $M_j$ to be the value of $M_{ref}$.

4. A method as in claim 3 wherein step (b) comprises illuminating the calibration target with actinic radiation that comprises x-rays.

5. A method as in claim 4 wherein the calibration target comprises a sheet of tungsten.

6. A method as in claim 5 wherein the sheet of tungsten comprises an orificethat is a right isosceles triangle.

7. A method as in claim 3 wherein steps (a), (b), (c) and (d) further comprise the respective steps of transporting, illuminating, collecting and storing for a workpiece comprising a printed circuit assembly and a step (i) of forming reconstructed images thereof at selected values of $z_i$ by using shifts and accumulation upon $Y\alpha@X_i$ and $X\alpha_i@Y_i$ that are thus formed.

8. A method as in claim 7 wherein step (b) comprises illuminating the workpiece with actinic radiation that comprises x-rays.

9. A method as in claim 7 wherein the workpiece is transparent to at least some wavelengths of visible light and wherein step (b) comprises illuminating the workpiece with visible light.

10. A method as in claim 3 wherein the plurality of multiple element sensors comprises a generally circular arrangement of multiple element sensors disposed upon the detection plane at known locations relative to each other.

11. A method as in claim 3 wherein the plurality of multiple element sensors comprises a regular arrangement of multiple element sensors disposed upon the detection plane at known locations relative to each other, and wherein the regular arrangement comprises the vertices of a regular geometric figure.

12. A method as in claim 3 wherein the plurality of multiple element sensors comprises an arbitrary arrangement of multiple element sensors disposed upon the detection plane at known locations relative to each other.

13. A method as in claim 3 wherein step (a) comprises motion in a serpentine pattern having legs parallel to the y direction and that are each a step apart in the x direction.

14. A method as in claim 3 wherein the plurality of multiple element sensors comprises time domain integration sensors.

* * * * *

UNITED STATES PATENT AND TRADEMARK OFFICE
CERTIFICATE OF CORRECTION

PATENT NO. : 7,309,161 B1  Page 1 of 1
APPLICATION NO. : 11/552545
DATED : December 18, 2007
INVENTOR(S) : Eliasson It is certified that error appears in the above-identified patent and that said Letters Patent is hereby corrected as shown below:

On the face page, in field (57), under "Abstract", in column 2, line 12, delete "calibrations" and insert -- calibration --, therefor.

On the face page, in field (57), under "Abstract", in column 2, line 16, delete "$z_y$." and insert -- $z_x$–$z_y$. --, therefor.

In column 11, line 32, in Claim 2, after "as" insert -- in --.

In column 12, line 37, in Claim 7, delete "accumulation" and insert -- accumulations --, therefor.

In column 12, line 37, in Claim 7, delete "$Y\alpha$" and insert -- $Y\alpha_i$ --, therefor.

Signed and Sealed this

Twenty-fourth Day of June, 2008

JON W. DUDAS
*Director of the United States Patent and Trademark Office*